(12) United States Patent
Hahn

(10) Patent No.: US 6,890,176 B2
(45) Date of Patent: May 10, 2005

(54) INTERPROXIMAL MATRIX WITH ELASTOMERIC WEDGE

(76) Inventor: Christian W. Hahn, 205 Avenida de la Grulla, San Clemente, CA (US) 92672

( * ) Notice: Subject to any disclaimer, the term of this patent is extended or adjusted under 35 U.S.C. 154(b) by 112 days.

(21) Appl. No.: 10/179,448

(22) Filed: Jun. 26, 2002

(65) Prior Publication Data

US 2003/0186186 A1 Oct. 2, 2003

Related U.S. Application Data

(60) Provisional application No. 60/324,129, filed on Sep. 20, 2001.

(51) Int. Cl.$^7$ .............................. A61C 5/04; A61C 7/00
(52) U.S. Cl. ......................................... 433/39; 433/149
(58) Field of Search .......................... 433/39, 148, 149

(56) References Cited

U.S. PATENT DOCUMENTS

| | | | |
|---|---|---|---|
| 804,099 A * | 11/1905 | Chase | 433/163 |
| 2,090,904 A * | 8/1937 | Singer | 433/148 |
| 2,150,005 A * | 3/1939 | McNinch | 433/149 |
| 3,020,638 A | 2/1962 | Tofflemire | 433/155 |
| 3,795,052 A * | 3/1974 | Mowery | 433/39 |
| 5,342,197 A | 8/1994 | Stein et al. | 433/154 |
| 5,607,302 A | 3/1997 | Garrison et al. | 433/39 |
| 5,622,496 A | 4/1997 | Champagne | 433/39 |
| 5,788,487 A | 8/1998 | Meyer | 433/39 |
| 5,788,491 A | 8/1998 | Shaw | 433/155 |
| 5,890,901 A | 4/1999 | Fischer et al. | 433/149 |
| 5,975,906 A | 11/1999 | Knutson | 433/226 |
| 6,074,210 A | 6/2000 | Garrison | 433/149 |
| 6,142,778 A | 11/2000 | Summer | 433/39 |
| 6,293,796 B1 | 9/2001 | Trom et al. | 433/155 |
| 6,336,810 B1 | 1/2002 | Bertoletti | 433/39 |
| 6,435,874 B1 * | 8/2002 | Hughes | 433/149 |
| 6,619,956 B1 * | 9/2003 | Weir | 433/39 |

* cited by examiner

Primary Examiner—John J Wilson
(74) Attorney, Agent, or Firm—Myers Dawes Andras & Sherman, LLP

(57) ABSTRACT

A dental apparatus adapted to facilitate formation of a filling in an object tooth and to retain the filling within normal boundaries of the object tooth and generally spaced from an adjacent tooth includes a matrix having a resilient wedge member attached thereto. The resilient wedge member is elongated and has enlargements at opposite ends thereof. In use, the resilient wedge member is stretched. While the resilient wedge member is in the stretched state, the matrix and resilient wedge member are placed together between the object tooth and an adjacent tooth. The resilient wedge member is then released and contracts toward its natural unstretched state. As the resilient wedge member contracts, it urges the matrix to surroundingly conform to the object tooth. In this way, a tooth is comfortably and conveniently prepared to receive a filling.

24 Claims, 3 Drawing Sheets

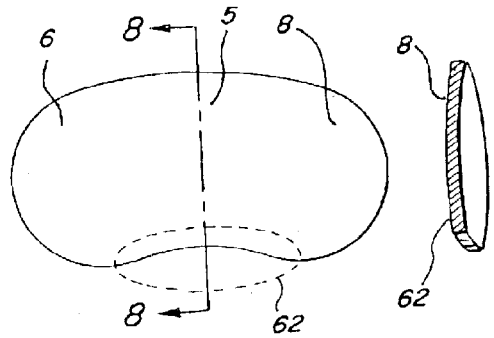
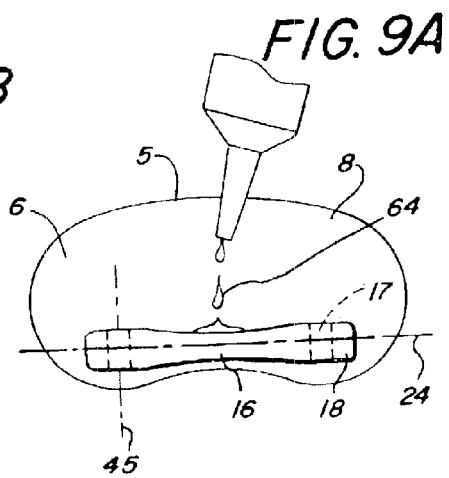
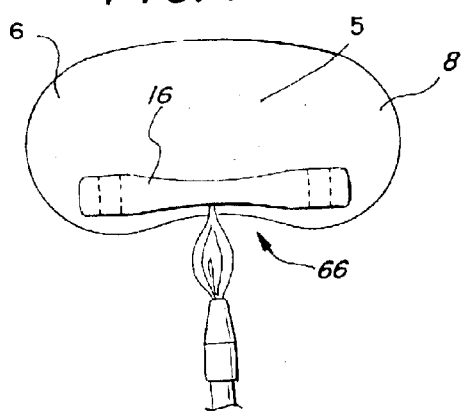
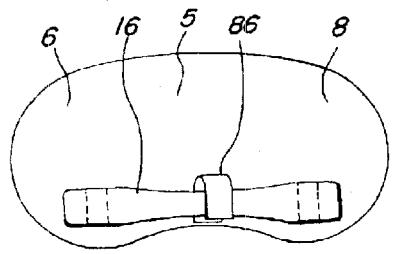
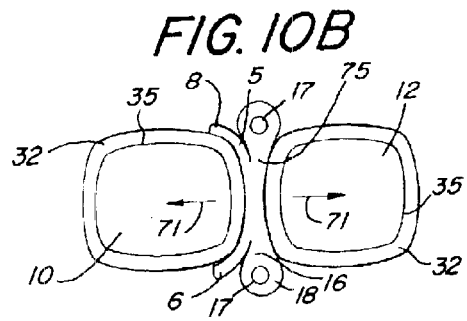
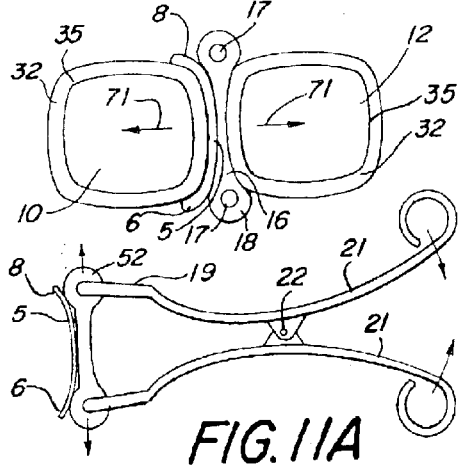
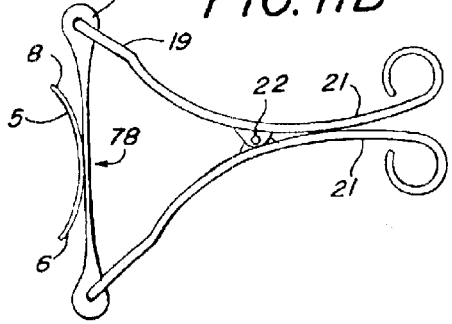

INTERPROXIMAL MATRIX WITH ELASTOMERIC WEDGE

CROSS REFERENCE TO APPLICATIONS

This is a non-provisional patent application claiming the priority of provisional application Ser. No. 60/324,129, filed Sep. 20, 2001, and entitled "Metal Shim With Attached Rubber Wedge", which is incorporated herein by reference.

BACKGROUND OF THE INVENTION

1. Field of the Invention

The instant invention relates generally to the field of dentistry, and more specifically to matrices, wedges, and methods of using the same.

2. Description of the Prior Art

Systems of the past have been used to close off a hole or trench made for the purpose of receiving a filling in an object tooth. Such a trench needs to be closed off when it extends to an outer periphery of the tooth in order to prevent flow of the filling material to the adjacent tooth. Thus, in filling a tooth, a dentist often uses a shim or matrix to block the flow of a filling material from an object tooth. As such, the matrix is utilized to retain the filling within the normal boundaries of the object tooth where it is generally spaced from the adjacent tooth.

Matrices of the past comprise generally flat barriers that are held against the object tooth and gums by small wooden or plastic wedges. These wedges are difficult to use, cause discomfort or pain, and tend to damage the tissue of the gums. Furthermore, since the matrices of the past tend to be relatively rigid, they do not adequately seal the gingival margin along the tooth. Thus, the wedge and matrix combinations of the past are deficient in providing an adequate seal with the tooth, in avoiding damage to the gum tissue, in providing a comfortable treatment for the patient, and in assuring sealing of the gingival margin.

An alternative to wedge-type devices is a spring-loaded matrix system ring, which may or may not be used in conjunction with the wedges described above. The spring-loaded matrix system uses rings to clamp the matrix on an end face of a tooth. Once again, these rings are expected to provide both sealing and stabilization of the matrix. The degree to which these rings effectively seal the gingival margin depends upon the angle at which tines of the rings engage the matrix. Furthermore, these rings act as rather stiff springs and are hard and abrasive. Thus, the spring-loaded matrix systems of the past fall short of what is required because they do not adequately provide a comfortable and consistent means for holding the matrix in a surrounding relationship to the tooth.

Both of the systems mentioned above are rather unnatural and can be highly irritating to the gum tissues. The elements utilized in the systems are hard and highly invasive. Thus, the prior art is deficient in providing a soft, effective, and comfortable means for supporting the matrix in a consistently sealed relationship with the tooth.

As can be appreciated, both of the means for stabilizing and sealing a matrix discussed above are directed more to point-type supports. They each support the matrix against the tooth and gums of the patient at specific points or locations on the matrix. As such, the systems of the past are deficient in providing a flexible hoop-type support that applies forces to a matrix along a continuous line. These systems of the past require a plurality of individual pieces and many steps in the placement process.

SUMMARY OF THE INVENTION

The dental apparatus of the instant invention overcomes the deficiencies of the past and provides a comfortable and effective means for stabilizing the matrix and for sealing the gingival margin throughout a length of the area to be treated. In short, a resilient wedge member of the instant invention fulfills a need and overcomes deficiencies with a structurally distinct apparatus. Furthermore, the method of placement is greatly simplified in comparison with the methods of the past, which employed wedges and rings.

The dental apparatus of the instant invention is adapted to facilitate formation of a filling in an object tooth and to retain the filling within normal boundaries of the object tooth and generally spaced from the adjacent tooth. The apparatus includes a thin sheet shim or matrix for at least partially surrounding the object tooth and for fitting between the object tooth and the adjacent tooth. A wedge member is connected to the matrix, and includes a pair of wedges joined by a central segment. At least one of the central segment and the pair of wedges of the wedge member is formed of an elastomeric material. In most cases, the central segment of the wedge member is elastomeric and is attached to a lower central portion of the matrix.

Alternatively, at least one of the wedges is elastomeric and the central segment of the wedge member comprises a portion of the matrix. In this case, a pair of wedges is attached to at least a pair of respective locations on a lower central portion of the matrix.

The instant invention is also embodied as a matrix and dental wedge system adapted to facilitate formation of a filling in an object tooth and to retain the filling within the generally normal boundaries of the object tooth, generally spaced from an adjacent tooth. The wedge member and matrix are selectively placed between teeth by selectively using a mounting tool.

In a very simple form, the interproximal matrix is formed of a sheet material having rounded surfaces. The resilient wedge member has a pair of enlargements and the resilient wedge member is attached to the interproximal matrix for insertion therewith between two adjacent teeth.

A method of using the interproximal matrix and an attached resilient wedge member of the instant invention is described herein. It should be noted that the method of use of the instant invention is particularly beneficial in simplifying a class II composite restorative procedure, and in reducing any tissue trauma and discomfort experienced by a patient. Other procedures utilizing flowable or packable substances for fillings may also be benefited by the instant invention. The method includes stretching the resilient wedge member to narrow a middle portion thereof. Then the middle portion and the interproximal matrix are moved between two adjacent teeth. Next the gums and the teeth of a patient are engaged with the matrix and resilient wedge member by releasing the mounting tool.

In another aspect of the method, the step of engaging further includes sealing a gingival margin of the object tooth. At the same time, the matrix is completely conformed to the object tooth and the gums. Furthermore, the object tooth is surrounded on one side and on parts of two other sides by the matrix by a biasing resilience of the resilient wedge member similar to a flexible hoop or noose.

The method is generally accomplished by causing the resilient wedge member to temporarily simulate a piece of dental floss by the step of stretching. While in the stretched state, the resilient wedge member and matrix are placed between two adjacent teeth. Then the resilient wedge member is released. The resilient wedge member thus contracts and provides the sealing and stabilizing by the single action. Thus, supporting and sealing a matrix on an object tooth is minimally invasive. That is, supporting and sealing a matrix on an object tooth according to the instant invention is approximately as invasive as is flossing between two teeth.

These and other features and advantages of the invention will be better understood with a discussion of preferred embodiments and reference to the associated drawings.

DESCRIPTION OF THE DRAWINGS

FIG. 7 is an end elevation view of the matrix part of the appliance;

FIG. 8 is a sectional view along lines 8—8 of FIG. 7;

FIGS. 9A–9C are end elevation views depicting different attachment means;

FIG. 10A is a section view taken along the lines 10A—10A of FIG. 3 with teeth separation exaggerated to slow a two-piece embodiment;

FIG. 10B is a section view similar to FIG. 10A with teeth separation exaggerated to show a one piece alternative embodiment; and FIGS. 11A and 11B are top plan views illustrating use a clamp to open/stretch a resilient wedge member.

DESCRIPTION OF THE PREFERRED EMBODIMENTS AND BEST MODE OF THE INVENTION

Figure 1A:
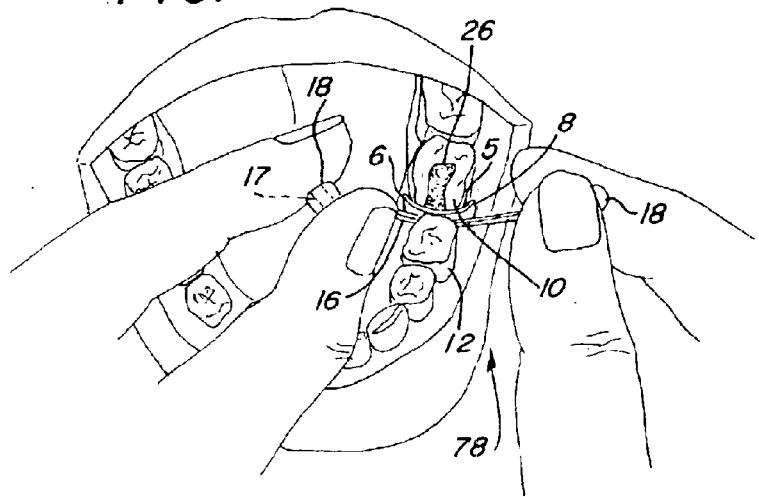
FIG. 1A is a perspective top view of a matrix/wedge appliance of the instant invention, being applied in the mouth of a patient.

As depicted in FIG. 1A, an interproximal shim or matrix 5, having first and second ends 6, 8, is to be placed between a first object tooth 10 and a second adjacent tooth 12. The matrix 5 forms a barrier around a portion of first tooth 10. Advantageously, the instant invention will typically include a resilient wedge member 16 in combination with the matrix 5. The resilient wedge member 16 has through holes 17 in opposing enlarged end portions 18 of the resilient wedge member 16. The through holes are provided for aiding in gripping the end portions 18 of the resilient member 16. FIG. 1A shows how the resilient wedge member 16 works together with the matrix 5 in locating and stabilizing the matrix 5 between the two teeth 10, 12.

Figure 1B:
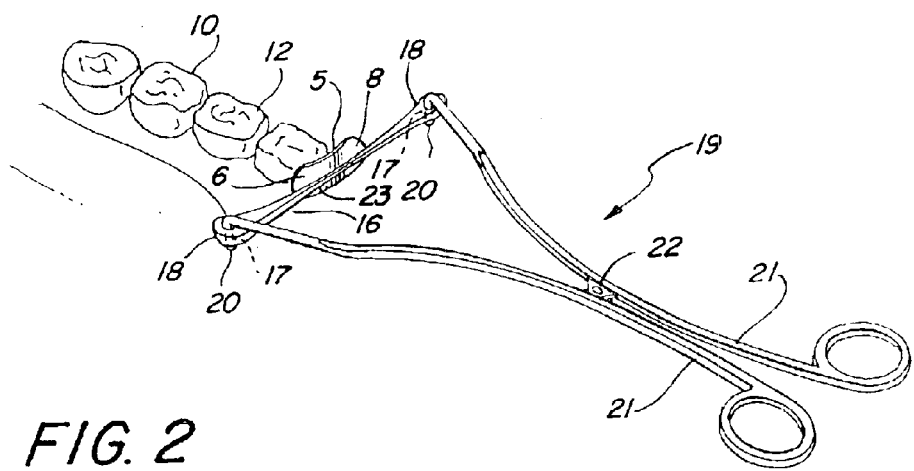
FIG. 1B is a perspective view similar to FIG. 1A depicting implementation of the appliance utilizing a mounting tool.

While FIG. 1A depicts placement of the matrix 5 and resilient wedge member 16 by hand, it is to be understood that the same placement is advantageously accomplished with a mounting tool 19. The mounting tool 19 has prongs 20 that engage the through holes 17 and stretch the resilient wedge member 16 when handles 21 are grippingly pushed together as shown in FIG. 1B. Use of the mounting tool 19 has the advantage of enabling easier access into the tight quarters of a patient's mouth. Furthermore, a user can grip the tool 19 with one hand and still have his or her other hand free. The mounting tool 19 provides mechanical advantages that aid in stretching and maintaining the resilient member 16 in a stretched condition. The mounting tool 19 provides these advantages by providing a fulcrum 22 against which the force bearing members of the tool can constantly be braced and by the configuration of the tool 19 enabling operation with the fingers of the user moved to a nearly completely closed position.

Figure 2:
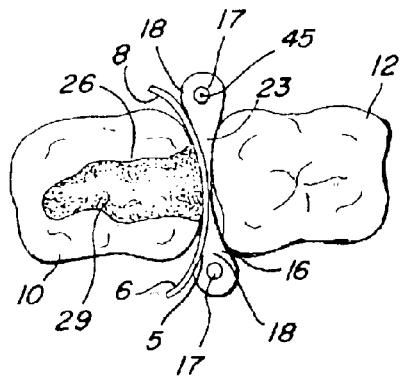
FIG. 2 is a top plan view of the appliance inserted between two adjacent teeth with one tooth having received a restoration material.

As shown in FIG. 2, the wedge member 16 is generally elongated, and the central segment 23 is a narrow central segment that fits between teeth 10, 12. The wedges are provided by respective enlarged ends 18 of the elongated wedge member 16, and portions of at least one of the wedges define a gripping hole 17. The wedge member comprises a resilient and conforming material such that when the matrix 5 and the wedge member 16 are moved between the adjacent teeth 10, 12 and released, the wedges push the ends 6, 8 of the matrix 5 around the object tooth 10 in a partially surrounding relationship as shown in FIGS. 2 and 3.

As can be noted from FIGS. 1A–3, the matrix 5 and wedge member 16 of the instant invention function very differently from systems of the past that were used for the same purposes. Advantageously, the resilient wedge member has a stretched state and the contracted state. When moving toward the stretched state, the distance between enlargements 18 is increased. Furthermore, the thickness of any elastomeric material interconnecting the enlargements 18 is reduced. This permits unobstructed placement of the matrix 5 and the resilient wedge member 16 between the adjacent teeth 10, 12. On the other hand, the distance between the enlargements 18 is reduced as the wedge member 16 resiliently moves from the stretched state to the contracted state so that opposite inward forces are applied to the adjacent teeth 10, 12 substantially in the direction of an axis 24 through the enlargements.

Furthermore, since the enlargements 18 progressively broaden in directions away from each other along the axis 24 through the enlargements, they sweep out a progressively broader path than the rest of the resilient wedge member 16 as they move toward each other from the stretched state to the contracted state. Thus, due to this broadening structure of the enlargements 18 and the resilient action of the elastomeric material utilized, forces are applied to the adjacent teeth 10, 12 in substantially transverse directions relative to the axis 24 through the enlargements 18 as well.

Figure 3:
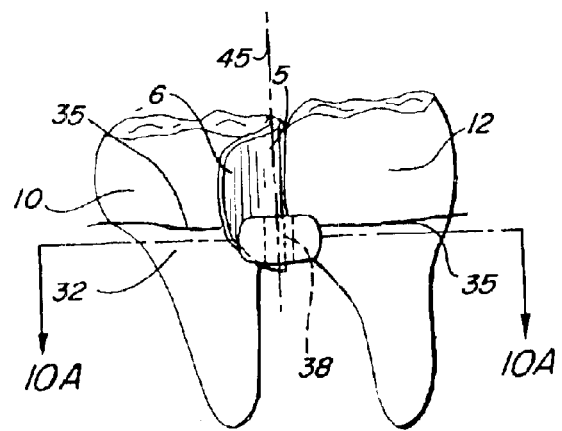
FIG. 3 is a side elevation view of the two adjacent teeth of FIG. 2 with the appliance inserted between the teeth.

As can be appreciated by viewing FIGS. 2 and 3, the resilient wedge member 16 of the instant invention conforms the matrix 5 nicely to the tooth 10 and seals the opening or trench 26. With the matrix 5 held in position by the resilient wedge member 16, the opening 26 is ready to be filled by filling material 29 in the class II composite restorative procedure.

FIG. 3 shows teeth 10, 12 protruding from gums 32. Considering the gingival margin 35 located generally at the boundary where the teeth 10, 12 protrude from the gums 32 is important in the instant invention because it presents a discontinuity in the surface engaged by the matrix 5. As set forth above, it has proven difficult to properly seal this discontinuity with the devices of the past. Furthermore, the tissues at the gingival margin 35 are vulnerable and can be easily damaged by the wedges of the past. As shown in FIG. 3, the matrix 5 and wedge member 16 tightly and resiliently seal off this gingival margin.

Figure 4:
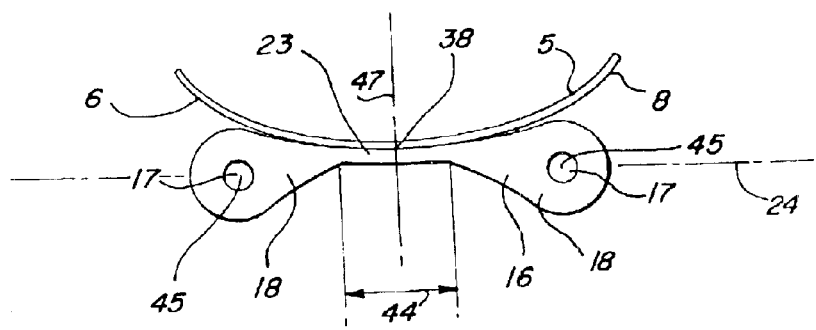
FIG. 4 is a top plan view of the appliance of the instant invention.

In the preferred embodiments, the resilient wedge member 16 is attached to the matrix 5 at a single location 38 as shown in FIG. 4. Alternatively, the wedge member may be attached at a plurality of locations as indicated at 41 in FIG.

5. Plural attachment locations could be applied to the embodiment of FIG. 4 as well. Other important structure is also shown in FIG. 4 including the narrow central segment 23, which joins the wedge shaped enlarged portions 18. Through holes 17 are provided in the enlarged portions 18 as shown in FIG. 4.

The general shape of the resilient wedge member 16 is elongate. As shown in FIG. 4, the narrow central portion 23 has a length 44 of approximately 2 mm. The narrow central portion 23 and the enlarged end portions 18 extend along a longitudinal axis 24. The through holes 17 are centered on through hole axes 45. As shown in FIG. 4, the enlarged end portions 18 are generally mirror images of each other relative to a mirror plane 47.

Figure 5:
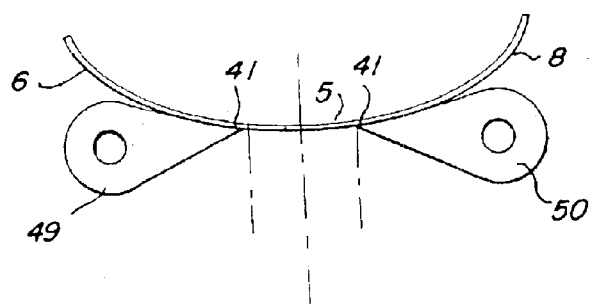
FIG. 5 is a top plan view showing an alternative embodiment having plural attachment locations of separate poles.

The enlarged portions 49, 50 of the embodiment of FIG. 5 likewise are mirror images of each other relative to a mirror plane 51. As shown in FIG. 5, the enlarged portions 49, 50 in this embodiment are formed as two separate pieces. In this embodiment, there is no additional thickness added by the resilient wedge member at a central portion of the matrix 5. As can be appreciated, this embodiment will be inserted between a pair of teeth in a similar fashion to the embodiment of FIG. 4. The enlarged portions 49, 50 are spaced similarly from each other and will function substantially the same as those of FIG. 4. However, the central segment that connects the enlarged portions 49, 50 comprises a portion of the matrix 5 as shown in FIG. 5. In most cases the matrix 5 is not elastomeric or stretchable. Hence, stretching is generally enabled in the embodiment of FIG. 5 by forming the enlarged portions 49, 50 of an elastomeric material. As can be appreciated, in an embodiment having a non-stretchable matrix 5 and the elastomeric enlarged portions 49, 50, most of the stretching will occur in a middle portion of the device, where the smaller cross-section regions of the enlarged portions 49, 50 approach the points of attachment 41.

Figure 6A:
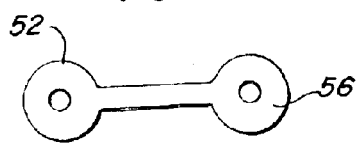
FIGS. 6A–6F are top plan views showing a variety of configurations of the resilient wedge member of the instant invention.
Figure 6D:
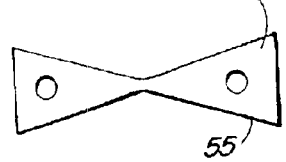
Figure 6B:
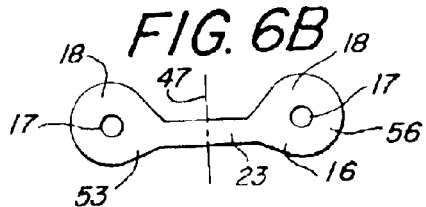
Figure 6E:
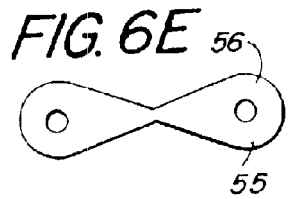
Figure 6C:
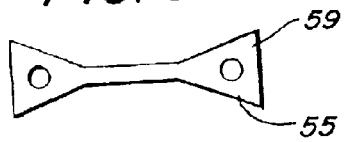
Figure 6F:
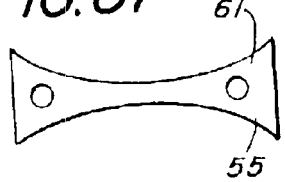

The resilient wedge member of the instant invention may take any of a variety of shapes and forms. A few such shapes are shown in FIGS. 6A through 6F. For example, FIG. 6A shows a barbell shape 52. FIG. 6B shows a bone shape 53. FIGS. 6C through 6F illustrate a bow tie shape 55. Similarly, the enlarged portions 18 may incorporate a variety of shapes. For example, FIGS. 6A, 6B, and to 6E have rounded end portions 56. The enlarged portions of FIG. 6D have triangular or wedge shapes 58. The enlarged portions 59 shown in FIG. 6C and the enlarged portions 56 of FIG. 6E have wedge shapes. The enlarged portions 61 shown in FIG. 6F have a concave triangular shape.

As set forth above, the interproximal matrix 5 has been used in combination with prior art wedges. The prior art wedges are typically small separate wooden wedges. The instant invention, on the other hand, provides for a resilient wedge member 16 attached to the matrix 5. FIGS. 7 and 8 indicate a location 62 on a lower portion of the matrix 5 to which the resilient wedge member 16 is attached in the instant invention.

FIGS. 9A through 9D show a variety of ways in which the resilient wedge member 16 may be attached to the matrix 5. In FIG. 9A, for example, the resilient wedge member 16 is being attached with glue 64. In FIG. 9B, the resilient wedge member 16 is being attached by a heat treatment means as shown at 66. In FIG. 9C, the resilient wedge member 16 is attached by metallic clip 68. The resilient wedge member 16 may alternatively be molded together with the matrix 5. Any number of different molding processes may be implemented. There are also a number of the other fastening means including combinations of those described herein, which are considered to be functional equivalents to those shown in FIGS. 9A through 9C. However, each of the means for attaching the matrix 5 to the resilient wedge member 16 has its particular advantages.

FIG. 10A is a section view taken along lines 10A—10A of FIG. 3. This sectional view shows how the matrix 5 and resilient wedge member 16 not only conform to the tooth 10 but also to the gums 32 substantially at the gingival margin 35. The resilience and constant pressure from the resilient wedge member 16 ensures that the matrix 5 substantially seals the gingival margin 35 and gums 32. This conforming force acting substantially normal to the tooth along a continuous line is achieved even without a complete circuit surrounding the tooth. This is due to the resilient nature and enlarged ends 18 of the wedge member 16. Also apparent in FIG. 10A is the separating force 71 which tends to force teeth 10, 12 away from each other.

The resilient wedge member 16 simultaneously seals the gingival margin 35, stabilizes the matrix 5, and forces to teeth 10, 12 away from each other. These actions are accomplished by a single action of the resilient wedge member 16. The net forcing of the teeth 10, 12 away from each other is due, in part, to the cancellation of the equal and opposite forces experienced by the enlargements 18 in their contracted state as they engage the teeth 10, 12 and gums 32. These equal and opposite forces are generally along the axis 24 of the elongated resilient wedge member 16.

FIG. 10B is similar to FIG. 10A. However, in this case, the matrix 5 and the resilient wedge member 16 are integrally formed as one-piece 75. Forming the matrix 5 and the resilient wedge member 16 as one-piece 75 has the advantage of reducing the number of steps required to make the device.

In one aspect of the method, best illustrated in FIG. 1A, the step of moving the matrix 5 and resilient wedge member 16 between the teeth includes placing the matrix with a concave portion thereof toward the object tooth 10 to be treated. This step also entails placing the resilient wedge member 16 on a side of the matrix 5 opposite to the object tooth 10.

FIGS. 11A and 11B show the mounting tool 19, which aids in the method of using the instant invention. As can be seen, when the handles 21 are squeezed, the resilient wedge member 52 is stretched. In the case of a stretched configuration, the combination matrix 5 and resilient wedge member 52 is ready to be placed between two adjacent teeth. In the stretched configuration, the resilient wedge member 52 is in the simulated dental floss configuration 78. Simulated dental floss 78 is also achieved with the resilient wedge member of the other embodiments as shown in FIG. 1A.

The invention has been discussed with particular reference to the figures and other alternatives. However, it is to be explicitly understood that there are a wide variety of variations of the invention not specifically disclosed herein, but which fall within the spirit and scope of the invention. Hence, the scope of the invention is to be limited only in accordance with the claims that follow.

I claim:

1. A dental apparatus adapted to facilitate formation of a filling in an object tooth and to retain the filling within normal boundaries of the object tooth and generally spaced from an adjacent tooth, including:
    a thin sheet matrix for at least partially surrounding the object tooth and for fitting between the object tooth and the adjacent tooth;
    a wedge member connected to the matrix, and including a pair of wedges joined by a central segment; and
    at least a portion of the wedge member being formed of an elastomeric material.

2. The dental apparatus of claim 1, wherein the central segment of the wedge member is elastomeric and is attached to the matrix.

3. The dental apparatus recited in claim 2, wherein the central segment of the wedge member is attached to a lower central portion of the matrix.

4. The dental apparatus of claim 1, wherein at least one of the wedges is elastomeric and the central segment of the wedge member comprises a portion of the matrix.

5. The dental apparatus of claim 4, wherein the pair of wedges are separately attached to a lower central portion of the matrix.

6. The dental apparatus recited in claim 1, wherein:
the wedge member is elongated;
the central segment is narrow relative to the wedges;
the wedges are formed as respective enlarged ends of the elongated wedge member; and
portions of at least one of the wedges define a gripping hole.

7. The dental apparatus recited in claim 6, wherein:
the wedge member has one of a barbell, a bone, or a bow tie shape; and
the enlarged ends have at least one of a rounded, a wedged, or a concave shape.

8. The dental apparatus recited in claim 6, wherein the central segment of the wedge member is approximately 2 mm in length in a natural, contracted state.

9. The dental apparatus recited in claim 6, wherein:
the matrix has first and second ends; and
the wedge member comprises a resilient material having properties for enabling the matrix and the wedge member to be moved between the adjacent teeth with the wedge member in a stretched state, and properties for pushing the first and second ends of the matrix around the object tooth in a partially surrounding relationship in a contracted state.

10. The dental apparatus recited in claim 1, wherein:
the wedges comprise first and second opposing enlargements; and
the central segment of the wedge member has a first end connected to the first enlargement and a second end connected to the second enlargement.

11. The dental apparatus of claim 10, wherein:
the first and second enlargements and the central segment are configured to form one of a barbell, a bow tie, and a bone shape; and
the enlargements have one of a generally rounded and concave shape.

12. The dental apparatus of claim 10, wherein:
the first enlargement is a mirror image of the second enlargement; and
the first and second enlargements are integral with the central segment.

13. The dental apparatus of claim 10, wherein:
the first enlargement is a mirror image of the second enlargement; and
the first and second enlargements are individually attached to the central segment.

14. The dental apparatus of claim 10, wherein the enlargements and the matrix are formed as a single appliance.

15. A combination including an interproximal matrix with a resilient wedge member adapted for insertion between two adjacent teeth, comprising:
the interproximal matrix being formed of a sheet material and having a convex surface;
the resilient wedge member having an axis and a pair of enlargements separated by a distance along the axis;
means for attaching the wedge member to the matrix to facilitate simultaneous insertion of the matrix and the wedge member between the two adjacent teeth;
the resilient wedge member being attached to the interproximal matrix by at least one of an adhesive, a heat treatment bond, a molding means, and a fastener;
the resilient wedge member being attached to a lower portion of the matrix in abutting relation to the convex surface of the matrix.

16. The combination of claim 15, wherein the resilient wedge member has a stretched state and a contracted state wherein:
the distance between the enlargements is increased when the resilient wedge member is moved from the contracted state to the stretched state to facilitate placement of the resilient wedge member and the attached matrix between the adjacent teeth;
the distance between the enlargements is reduced as the resilient wedge member moves from the stretched state to the contracted state to facilitate an application of force to the adjacent teeth;
each of the enlargements broadens with progressive positions away from the other enlargement along the axis; and
the enlargements are biased to move toward each other from the stretched state to the contracted state such that forces are applied to the adjacent teeth in substantially transverse directions relative to the axis of the wedge member.

17. A method for using an interproximal matrix and an attached resilient wedge member for simplifying a class II composite restorative procedure involving an object tooth and an adjacent tooth of a patient, comprising:
providing a wedge member having a middle portion;
narrowing the middle portion of the wedge member;
moving the middle portion of the wedge member and the interproximal matrix between two adjacent teeth; and
releasing the resilient wedge member to assert a separation force on the teeth of the patient.

18. The method of using of claim 17, wherein the step of moving further comprises:
placing the matrix with a concave portion thereof facing the object tooth; and
placing the resilient wedge member on a side of the matrix opposite to the object tooth.

19. The method using as claim 17, wherein the step of releasing further comprises:
sealing a gingival margin of the object tooth;
conforming the matrix to the object tooth and adjacent gums of the patient; and
during the conforming step, biasing the resilient wedge member to form the matrix against the object tooth.

20. The method of claim 19, wherein the step of surrounding further comprises closing off an opening or trench in the tooth for filling the tooth with a matrix.

21. The method of claim 17, further comprising simultaneously sealing a gingival margin and stabilizing the matrix by a single action of the resilient wedge member.

22. The method of claim 21, further comprising:
causing the resilient wedge member to temporarily simulate a piece of dental floss by the step of stretching; and
enabling the single action of the resilient wedge member by the step of releasing.

23. The method of claim 22, further comprising:
causing the resilient wedge member to temporarily simulate a piece of dental floss by the step of stretching; and
enabling the single action of the resilient wedge member by the step of releasing.

24. The method of claim 21, and further comprising simultaneously forcing the teeth away from each other by the single action of the resilient wedge member.

* * * * *